United States Patent [19]

Georges et al.

[11] 4,355,331
[45] Oct. 19, 1982

[54] X-RAY IMAGE SUBTRACTING SYSTEM

[75] Inventors: Jean-Pierre J. Georges, Waukesha; Gary S. Keyes, Hartland; William H. Wesbey, New Berlin, all of Wis.

[73] Assignee: General Electric Company

[21] Appl. No.: 229,249

[22] Filed: Jan. 28, 1981

[51] Int. Cl.³ .............................................. H04N 5/32
[52] U.S. Cl. ..................................... 358/111; 378/99
[58] Field of Search ............................. 358/111, 106; 250/416 TV

[56] References Cited

U.S. PATENT DOCUMENTS

3,974,386 8/1976 Mistretta et al. .................... 358/111
4,204,225 5/1980 Mistretta ............................. 358/111
4,204,226 5/1980 Mistretta et al. .................... 358/111

Primary Examiner—Richard Murray
Attorney, Agent, or Firm—Ralph G. Hohenfeldt

[57] ABSTRACT

An x-ray source projects successive high and low energy x-ray beam pulses through a body and the resultant x-ray images are converted to optical images. Two image pick-up devices such as TV cameras that have synchronously operated shutters receive the alternate images and convert them to corresponding analog video signals. In some embodiments, the analog signals are converted to a matrix of digital pixel signals that are variously processed and subtracted and converted to signals for driving a TV monitor display and analog storage devices. In other embodiments the signals are processed and subtracted in analog form for display. The high and low energy pulses can follow each other immediately so good registration between subtracted images is obtainable even though the anatomy is in motion. The energy levels of the x-ray pulses are chosen to maximize the difference in attenuation between the anatomical structure which is to be subtracted out and that which remains.

37 Claims, 8 Drawing Figures fig. 3 fig. 6 fig.5 fig.7

X-RAY IMAGE SUBTRACTING SYSTEM

BACKGROUND OF THE INVENTION

This invention relates to subtraction fluoroscopy and radiography.

Subtraction of x-ray images is a known method for making low contrast structures in the images more conspicuous. In ordinary x-ray images, the bone, blood vessels or other tissue of primary diagnostic interest may be surrounded or overlayed or underlayed by tissue or bone which obscures and prevents easy visualization of the structure of interest. The function of the subtraction process is to remove or suppress the potentially confusing effects of uninteresting overlying and underlying structures to thereby enhance the detectability of the structure of interest.

Image subtraction has been used in the past primarily for angiography, that is, for making x-ray examinations of blood vessels such as the vessels of the heart. In accordance with this technic, a radiographic or fluoroscopic x-ray image of the heart is made and recorded. The first image is called a mask. Shortly afterwards, an x-ray opaque medium, such as an iodine compond, that has been injected into the blood vessels reaches the vessels of interest and then another image is made. The blood vessels of interest in the pre-injection and post-injection images are almost always obscured by overlaying or underlying bone or other tissue, thus making visualization difficult. However, when the images are subtracted from each other, anatomical structures which cause confusion are deemphasized or substantially eliminated and a high contrast and more easily visualized image of the iodine-infused vessels remains.

Obtaining a mask image and one or more images in sucession at a relatively low rate is characterized as temporal subtraction. It is satisfactory for dealing with anatomy whose position is static or slowly changing but there is often a significant loss of registration between successive images when the vasculature of a rapidly moving organ such as the heart is being examined. This is manifested by blurring and loss of detail in the subtracted image. Even motion of anatomical regions due to such things as peristalsis and breathing can produce motion artifacts in temporally obtained subtraction images. For many applications, differentiation of low contrast anatomical structures can be obtained by acquiring images at two or more different x-ray energy levels. For instance, it is known that the mass attenuation coefficient of bone and soft tissue is much lower at an x-ray photon energy level corresponding with about 70 peak kilovolts (kVp) being applied to the x-ray tube than is the mass attenuation coefficient of iodine at the same energy level. It is also known that as one progresses up the energy scale such as to 135 or 140 kVp, the mass attenuation coefficient of soft tissue changes by a relatively small amount, but the iodine changes by a large amount. Thus, it has been proposed, as in co-pending application of L.S. Edelheit, Ser. No. 179,203, filed on Aug. 18, 1980, owned by the assignee of this application, to use an x-ray image intensifier for producing a quick succession of low and high kVp images. The successive images are viewed on the output phosphor of the image intensifier tube by a single video camera and the analog waveforms for each of the images are digitized and stored in separate memories. The picture elements (pixels) stored in corresponding locations in digitized form in the two memories are then combined to produce data for an image with enhanced contrast but with certain intensity levels, such as those due to bone and soft tissue of little interest, being suppressed. In this system, the single image pick-up tube or video camera which is used is blanked during x-ray irradiation and scanned or read out after each irradiation. However, the long time response of any video pick-up device relative to the time interval between exposures has a tendency to create overlapping images and would, by itself, lead to relatively poor quality subtracted or combined images.

A method of mitigating the problem involves scrubbing the video camera target plate during retrace time with a very high electron beam current. The beam deflection power necessary to scrub all previous raster lines in the one millisecond or so that is allowed, forbids such an approach with presently available standard video cameras. The use of time for scrubbing and reading imposes two limitations on the single image pick-up device system. First, the maximum image acquisition rate is about 10 frames per second. Second, the high and low energy x-ray pulses must be separated by at least two frame times or about 70 ms. Due to the substantial lapse of time between the high and low energy x-ray pulses, there is a greater likelihood that the anatomical structures will have moved so that undesirable loss of registration between pairs of subtracted or combined images mentioned earlier will occur. Furthermore, on some occasions, such as when the physician desires to watch progression of the opaque medium continuously and in real-time over an interval of twenty seconds or more or where the frame rate must be high enough to produce the effect of stopping heart motion, no time is available for scrubbing when a single pick-up device such as a video camera is used.

SUMMARY OF THE INVENTION

The invention disclosed herein is based on use of two image pick-up devices of any suitable type such as video cameras or charge-coupled image plates. In the illustrative embodiments, video cameras using electron beam readable image plates as pick-up devices are actually used. One camera is operative to obtain the image data for the image produced with a low x-ray tube peak kilovoltage (kVp) and the other is used to obtain the data for the image produced with a higher kilovoltage on the x-ray tube.

Systems are described for obtaining both static and dynamic images. Static images are those which can be obtained at a slow rate since only snapshots of the anatomy are required. In the described embodiments, progressive scanning and scrubbing of the image plate in the video pick-up device are used.

Dynamic imaging refers to obtaining a series of x-ray exposures where high and low energy x-ray pulses are close to each other in time and are alternated at a high rate for an extended period of time, up to 20 seconds, for example, the result being a series of subtracted images recorded at regular video or TV rates for real-time visualization of organs in motion. In the illustrated embodiments, interlaced video scans are employed such as to obtain thirty frames per second or submultiples thereof.

The image obtained with an x-ray pulse at one energy level becomes the mask for the image obtained with an x-ray pulse at the other energy level. The x-ray pulses have short durations. The second pulse can begin as soon as the first one in a pair ends. Since there is substantially no temporal delay between images, the anatomy can be in rapid motion and yet no loss of image registration will result. Analog and digital means are employed for developing weighted data for static or dynamic images, using two TV camera image pick-up means or other pick-up devices, as compared to the prior art practice of using a single pick-up device.

Thus, a primary object of the present invention is to provide an image subtraction system which is distinguished by using the pick-up means in two video cameras for respective high and low kilovoltage images. One benefit of the two camera system is that signal-to-noise ratios are improved by eliminating cross-talk between the high and low x-ray energy images so good subtraction images can be obtained even though differential attenuation of overlying, underlying or adjacent anatomical structures is small. Thus, in angiographic studies where an x-ray opaque medium is injected into the circulatory system, the medium can be very dilute and still permit obtaining subtraction images in which anatomical details are well contrasted and more easily visualized. Another benefit of this more sensitive subtraction method is that the low concentration and relatively small volume of x-ray opaque medium can be injected at a place in the circulatory system such as in a vein which is remote from the heart or other organ or tissue that is being examined.

Another object of the invention is to provide for processing the image data independently in each of two pick-up device channels so that the image or pixel data for the subtracted or combined images can be emphasized or deemphasized by signal addition, multiplication, subtraction and any other data modifying methods which increase the possibility of visualizing details in the displayed subtracted images.

Another important object is to provide for presenting x-ray images resulting from subtraction of weighted data in real-time at video rates so that blurring in the displayed image which might otherwise result from anatomical motion is significantly reduced and so motion, such as that of fluid flowing in blood vessels, can be observed over a long time interval.

How the foregoing and other more specific objects of the invention are achieved will be evident in the ensuing description of various embodiments of the plural camera system which will now be set forth in reference to the drawings.

DESCRIPTION OF THE DRAWINGS

FIG. 8 is a block diagram of an analog processor which is used in the systems.

DESCRIPTION OF PREFERRED EMBODIMENTS

Figure 1:
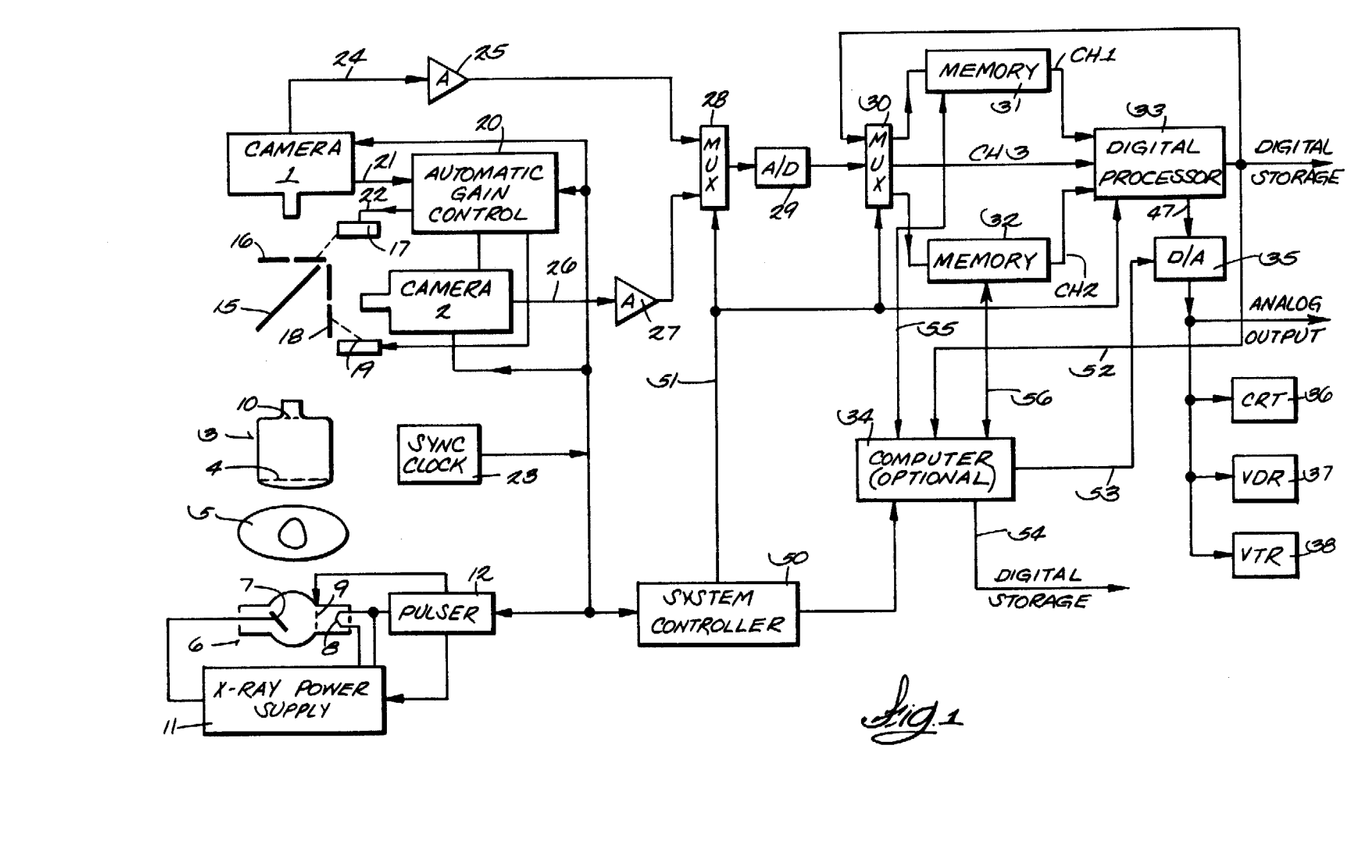
FIG. 1 is a functional block diagram of a two-channel static imaging system using digital subtraction methods and storage memories.

The system in FIG. 1 uses two pick-up devices which, in this embodiment, are video or TV cameras 1 and 2 that are so labelled. The x-ray image is produced with an electronic image intensifier tube that has an input screen symbolized by the dashed line marked 4. The body being subjected to an angiographic examination, for instance, is identified generally by the reference numeral 5. During examination, the body is disposed over the x-ray tube 6 which is conventional in that it comprises an anode target 7, a cathode or filament 8 and, in this particular example, a control grid 9. When the x-ray tube is energized, its beam is projected through body 5 to form a differentially attenuated x-ray image on the input screen 4 of image intensifier 3. The intensifier is conventional in that it converts the x-ray image to an electron image which is ultimately converted to a bright minified optical image on the output phosphor of the intensifier tube. The phosphor is symbolized by a dashed line marked 10.

The x-ray tube power supply is represented by the block marked 11. It is understood to provide high kilovoltage between anode 7 and cathod 8 for making an x-ray exposure. In this case it is to be understood that the x-ray power supply is capable of providing a low kVp and correspondingly low photon energy short duration pulse followed by a higher kVp and correspondingly higher photon energy pulse. By way of example and not limitation, typical pulse durations might lie in the range of about 1 to 6 ms. For the purposes of the invention and to minimize loss of registration due to anatomical motion during an imaging sequence, the low and high energy x-ray pulses in a pair follow each other with substantially no time between them. A long sequence of pulse pairs may be used for real-time imaging such as is employed when a moving organ is being viewed. The systems described herein are not restricted to having the low energy pulses preceed the high energy pulses.

The control for causing the x-ray tube to emit low and high energy pulses is represented by the block marked 12 which is identified as a pulser. A suitable pulser circuit is described in the co-pending application of Daniels et al, Ser. No. 208,095, filed Nov. 18, 1980, which is assigned to the assignee of the present application.

By way of example, when an iodine opaque medium is used for visualizing blood vessels by the subtraction method described herein, the low energy x-ray pulses have energy corresponding to about 70 kVp being applied between the anode and cathode of the x-ray tube and the highenergy pulses have energy corresponding to about 140 kVp being applied. The pulser in the co-pending application modulates the x-ray tube voltage and current by applying various bias voltages to the grid 9 of the x-ray tube. A control which switches the high voltage circuit of the x-ray tube could also be used.

In FIG. 1, an image splitter in the form of a semi-transparent mirror 15 is located in the optical path from output phosphor 10 of the image intensifier tube for directing images appearing on the phosphor toward video cameras 1 and 2. Camera 1 is provided with a shuttering device that is symbolized by the perforated line marked 16. Any suitable fast shutter such as a servoiris or rotating iris or shutter blade may be used. In an actual embodiment, a servo-shutter, which is known to those familiar with the photographic art, is used. The shutter is operated synchronously with occurrence of the x-ray pulses and the shutter driver for shutter 16 and camera 1 is symbolized by the block marked 17. When a low energy x-ray pulse occurs, servo-shutter 16 opens so that the image pick-up plate, not shown, in TV camera 1 will develop charge pattern corresponding to the image that is transmitted through image splitter 15 from the image intensifier. Maximum permissible opening of the camera irises is set at a point where no saturation of the image pick-up plate will result from the brightest image which is intercepted by the camera. This function is performed with an automatic gain control circuit represented by the block marked 20. This is a closed-loop gain control whereby, typically, signals representative of the brightness of the image received by a camera are transmitted by way of line 21 to the gain control and the gain control responds by providing a signal over line 22 which causes shutter control 17 to adjust the iris in the proper direction for limiting to a maximum permissible brightness.

The other image pick-up device in the form of video camera 2 is similar to camera 1. Camera 2 is also provided with a servo-shutter 18 and a driver 19. Camera 2 develops a charge pattern on its pick-up plate representing the image that results from the higher energy x-ray pulses. During a low energy x-ray pulse, shutter 16 for camera 1 is open and shutter 18 for camera 2 is closed. Conversely, during existence of a high energy pulse, shutter 18 for camera 2 is open and shutter 16 for camera 1 is closed.

Shutter operation, x-ray pulsing and image readout, that is, electron beam scanning of the image pick-up plate in the video camera and other operations in the system must be synchronized as is readily apparent. Synchronizing pulses may be obtained from either one of the cameras but to show their existence for the purpose of this discussion, they are indicated to be provided by a separate source represented by the clock marked 23 and labelled with the words "Sync Clock."

In FIG. 1, the analog video waveform signals are taken from camera 1 by way of a cable 24 which is connected to an input of an amplifier 25. The video waveform output from camera 2 is taken from it by way of a cable 26 which is connected to the input of another amplifier 27. Amplifiers 25 and 27 could be logarithmic amplifiers since logarithmic amplification is required and can be done either before or after digitization. For instance in digital processing, logarithmic amplification could be done in a digital processor which is part of the system and will be discussed later.

For static imaging, cameras 1 and 2 are preferably operated in the progressive scan mode rather than in an interlaced mode. Where only static or snapshot type images are being obtained at relatively infrequent intervals much time is provided for the camera image pick-up means to be electronically scrubbed between x-ray pulses. For static imaging, high and low x-ray pulse durations in the range of 1 ms to 20 ms are contemplated. The frame rate is limited by the sum of the x-ray pulse, camera readout, and scrubbing times. As indicated earlier, this may impose a limit of about 10 frames per second.

In FIG. 1, the video analog waveforms resulting from readout of the cameras are input to a multiplexer (MUX) represented by the block marked 28. The multiplexer is synchronously switched to deliver the analog signals from alternate cameras to an analog-to-digital (A/D) converter represented by the block marked 29. It converts the video analog waveform for each horizontal scan line from the camera pick-up means to corresponding digital values that represent image element or pixel intensities. The converter 29 outputs its digital pixel signals to a multiplexer represented by the block marked 30. This multiplexer switches the signals read out of one camera to a first memory or storage device 31 and switches the signals from the other camera to a second memory 32. Thus, memory 31 in channel 1 stores a new picture element matrix for each low energy x-ray pulse and the second memory 32 in a channel 2 stores a new picture element matrix each time a high energy x-ray pulse occurs. The multiplexers are, of course, switched synchronously with the exposure intervals of the cameras and, as has been implied, the A/D converter 29 is time-shared. In any event, shortly after a pair of low and high energy x-ray pulses occur, digital data corresponding with their respective images is stored in first and second memories 31 and 32.

In the FIG. 1 embodiment, a suitable digital processor represented by the block marked 33 is used to combine the weighted data representative of the low energy image in the first memory 31 with the weighted data for the high energy image in the second memory 32. The digital processor operates synchronously to withdraw the image data when they are available and performs a combination, such as a weighted subtraction, of the geometrically corresponding picture element signals in one memory from the other to yield a matrix of digital pixel data representative of the subtracted images. A more detailed description of the digital processor 33 will be presented soon. For the moment it is sufficient to recognize that data from digital processor 33 may be extracted in digital form for storage in a digital disk or take device provided the device can accept data at video rates.

A second option for digital storage uses a computer, represented by the block marked 34. If the computer chosen operates rather slowly, such as a minicomputer, compared to some more expensive and faster computers that are currently available, it may be limited to reading out memories 31 and 32 at relatively slow rates for additional processing or storage on digital disk or tape devices, not shown, by way of data bus 54. Data thus processed could also be placed back in one of the memories at a slow rate and subsequently read out by digital processor 33 at video rates for digital-to-analog conversion and analog display.

If a more sophisticated computer 34 is chosen that is sufficiently fast to process data at video rates as the digital processor does, then the computer can be used for additional processing such as smoothing, for example, at video rates. In this case, the digital data at video rates from the digital processor can be supplied to computer 34 by way of a video rate data bus 52 for additional processing. The processed data can then be sent by way of video rate bus 53 to the D/A converter 35 for conversion to analog video signals for storage or display. Use of any computer 34 should be understood to be optional. Having a computer in the system, besides performing the functions just discussed, makes it available for performing various control functions which can be advantageous.

The ditigal data within the processor 33, representative of the weighted subtracted images, are directed through a digital-to-analog converter 35 to produce analog waveforms which may then be displayed on the symbolically representative cathode ray tube 36 of a video monitor. The analog video waveforms may also be recorded on a video disk recorder 37 or a video tape recorder 38.

Figure 7:
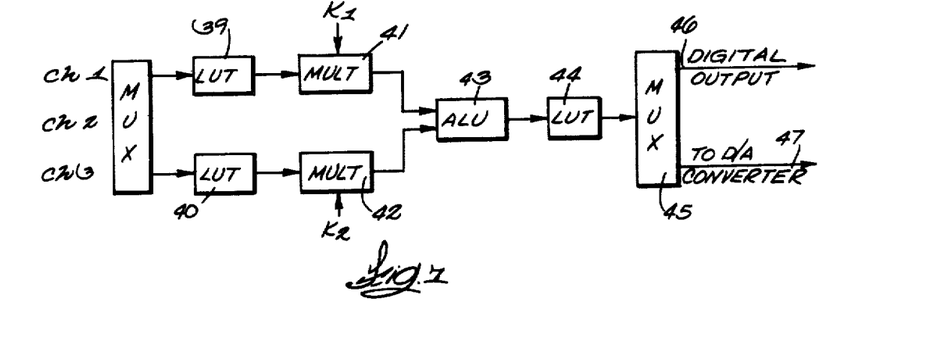
FIG. 7 is a block diagram of a digital processor used in the image subtraction system.

Components within a typical digital processor 33 for the FIG. 1 embodiment are shown in FIG. 7. The processor consists of three input channels Ch1, Ch2, and Ch3 normally associated with the two memories and the A/D converter 29 shown in FIG. 1. Each channel includes a digital look-up table (LUT) 39 and 40, respectively, and digital multipliers (MULT) 41 and 42. Multipliers 41 and 42 have additional inputs marked K1 and K2, respectively, for inputting selected constant factors for modifying or weighting the digital signals as required. Thus, subtracted images are not produced by simple subtraction, but by weighted linear combination of images from two energies that is $K_1I_1-K_2I_2$. Usually K will be a factor other than one. If it is one the image data, I, is still considered as being weighted in the context of this description and in the patent claims. In FIG. 7, weighted data from the two channels are combined, for example, subtracted in an arithmetic logic unit (ALU) 43 and subsequently modified in a third LUT 44 prior to being directed through a multiplexer 45 to a digital signal output port by way of a bus 46 or to a D/A converter, not shown, by way of a bus 47. All of the components within the digital processor are capable of operating at video rates so that data may be transmitted through the processor at at least thirty frames per second.

In order to maintain a constant signal level in the subtracted image of a particular x-ray opaque medium containing blood vessel, for example, through regions of changing anatomy, it is necessary that the subtraction be performed on the logarithms of the low and high energy image data. As indicated earlier, this can be accomplished either prior to digitization using analog logarithmic amplifiers 25 and 27 in FIG. 1 or it can be done after digitization using an LUT loaded with a logarithmic transformation function. The input LUTs 39 and 40 in the digital processor provide this capability. The multipliers 41 and 42 in the digital processor of FIG. 7 provide the means to perform a weighted subtraction between the low and high energy image data. The LUT following ALU 43 enables the difference or combined image data to be amplified to fill the dynamic range of the D/A converter 35 in FIG. 1 in order to minimize the impact of video electronic noise on the final analog image.

In FIG. 1, a system controller represented by the block marked 50 may be used to keep the various electronic components in the proper functional sequence. Typically, sequencing signals may be delivered over a bus 51 to the various components.

Figure 2:
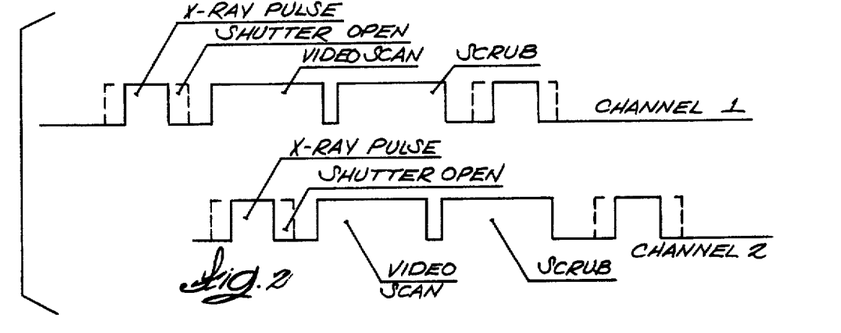
FIG. 2 is a timing diagram for describing the operation of the FIG. 1 system.

The timing sequence for producing the subtracted images with the FIG. 1 static imaging system is shown in FIG. 2. As can be seen, first a low energy x-ray pulse occurs during the interval in which shutter 16 is open. This charges the image pick-up plate of camera 1. At this time, the shutter to camera 2 in channel 2 is closed. When the low energy x-ray pulse and shutter opening of channel 1 is terminated, camera 1 is synchronized to begin its video scan readout in the progressive scan mode during the interval marked video scan on the channel 1 timing diagram in FIG. 2. During this time, the digitized scan data is being delivered to first memory 31 in FIG. 1. When the video scan after the progressive video scan or readout of camera 1 is completed, the image plate of this camera is scrubbed or charge equalized for the interval indicated in the channel 1 timing diagram. As can be seen in the channel 2 timing diagram, during the time that camera 1 is being scanned following a low energy x-ray pulse, the second or high energy x-ray pulse in a pair occurs while the shutter for camera 2 is open. As shown, as soon as the shutter for camera 2 is closed, its progressive video scan begins and this is followed by a scrubbing interval. During the respective progressive scans, the data derived therefrom is multiplexed alternately to memories 31 and 32 in FIG. 1. It should be apparent that the high energy x-ray pulse in channel 2 can occur at any time after the channel 1 pulse is terminated and shutter 2 opened. Progressive scan is permissible and desirable in static imaging since this is essentially a snapshot process.

It should now be evident that with the two pick-up means system herein disclosed, an important result has been achieved, namely, that the time interval between the high and low energy x-ray pulses is now limited only by the x-ray tube high voltage switching rate and the shutter speed and that the time interval is substantially independent of the characteristics of the cameras or pick-up devices.

Those skilled in the art will recognize that the synchronously switching A/D converter represented by the components MUX 28, A/D converter 29 and MUX 30 in the FIG. 1 embodiment could be replaced by two separate A/D converters for delivering the data for the low and high x-ray energy images from amplifiers 25 and 27 to the respective first and second memories 31 and 32.

The FIG. 1 system is meritorious in that it provides for complete versatility as far as x-ray pulse widths, pulse intervals, and video scanning times are concerned. By way of example, scanning of a 512×512 pixel matrix can be performed in 1/30th of a second or a 1024×1024 matrix can be scanned in 1/7.5 of a second using the same digitization rate. It should be noted however, that the FIG. 1 two pick-up device system requires a substantial amount of memory capacity and is most appropriate for making static type images.

Figure 3:
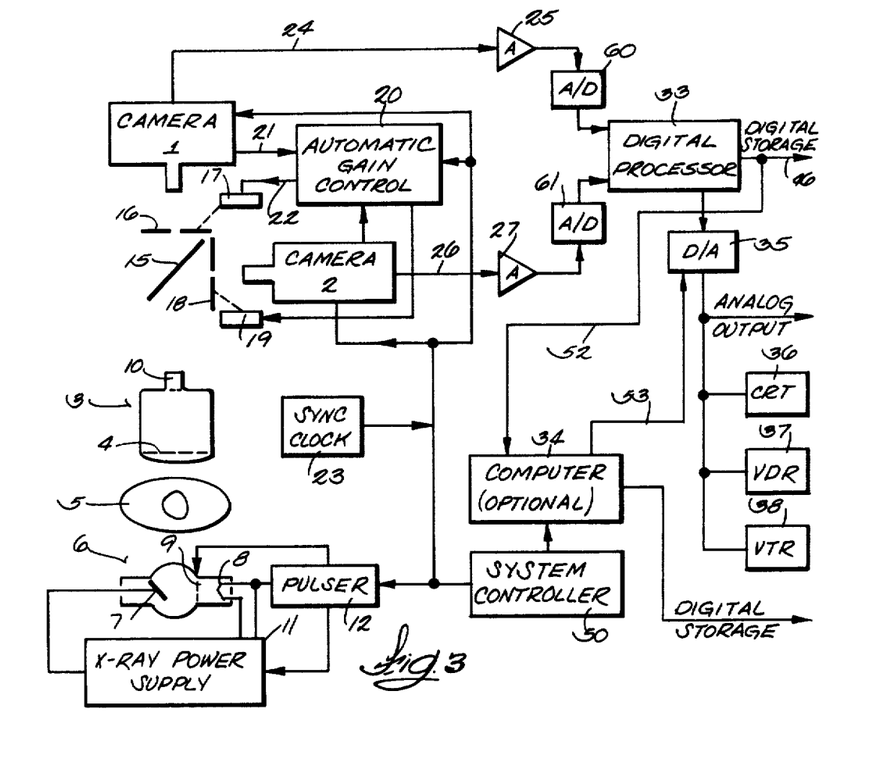
FIG. 3 is a functional block diagram of a two-channel digital subtraction system wherein the data are processed in digital form and no storage memories are used.

A dual channel and dual pick-up device x-ray image subtraction system which does not require use of large capacity individual dedicated memories or storage devices is depicted in FIG. 3. In this embodiment, parts which are similar to those in the FIG. 1 embodiment are given the same reference numerals. Since everything is the same up to the outputs of amplifiers 25 and 27 in FIG. 1, the components preceeding the amplifiers need not be described again. By using different timing schemes the FIG. 3 system is adaptable to static and dynamic imaging as will be discussed later.

In the FIG. 3 embodiment, the target or image pick-up plate of one of the cameras 1 and 2 at a time is used as a storage device. This permits elimination of memories 31 and 32 which were used in the FIG. 1 embodiment. In addition, two separate A/D converters 60 and 61 are used to deliver the low and high energy x-ray energy data directly to the input ports of the digital processor 33. The functions and architecture for the digital processor are identical to the processor in FIGS. 1 and 7, as are the remainder of the components in the FIG. 3 embodiment so they will not be described again. The timing diagram for the FIG. 3 system, when it is operated in the static imaging mode, is depicted in FIG.

4. As can be seen in respect to channel 1, after the low energy x-ray pulse is completed and the shutter for camera 1 is closed, the pick-up device in camera 1 remains blanked until the next high energy x-ray pulse is terminated and a charge image is accumulated on the plate or pick-up device in camera 2 as a result of its shutter being open while the high energy x-ray pulse is delivered. Now there are charge patterns representative of x-ray images stored on the image plates of each of the cameras. Then as can be seen in the FIG. 4 timing diagram, both cameras 1 and 2 are scanned or read out simultaneously in the progressive scan mode so the data for the high and low energy x-ray images is available at the same time. The video signals in the two channels are fed simultaneously through buses 24 and 26 to amplifiers 25 and 27, respectively, after which they are input to the respective A/D converters 60 and 61. The digital pixel signals output from converters 60 and 61 are input to digital processor 33 where they are weighted and combined or subtracted or otherwise processed as previously described.

The resulting subtracted image is then available in digital form on a bus 46 for digital storage on digital tape or disk. Digital pixel data output from processor 33 is also sent through D/A converter 35 for conversion to analog form for displaying on the cathode ray tube 36 of a video monitor or for recording in video disk recorder 37 or video tape recorder 38.

As will be discussed later, the FIG. 3 embodiment can also be used for dynamic or motion imaging provided the timing of events is in accordance with FIG. 6 as will also be discussed later.

Figure 5:
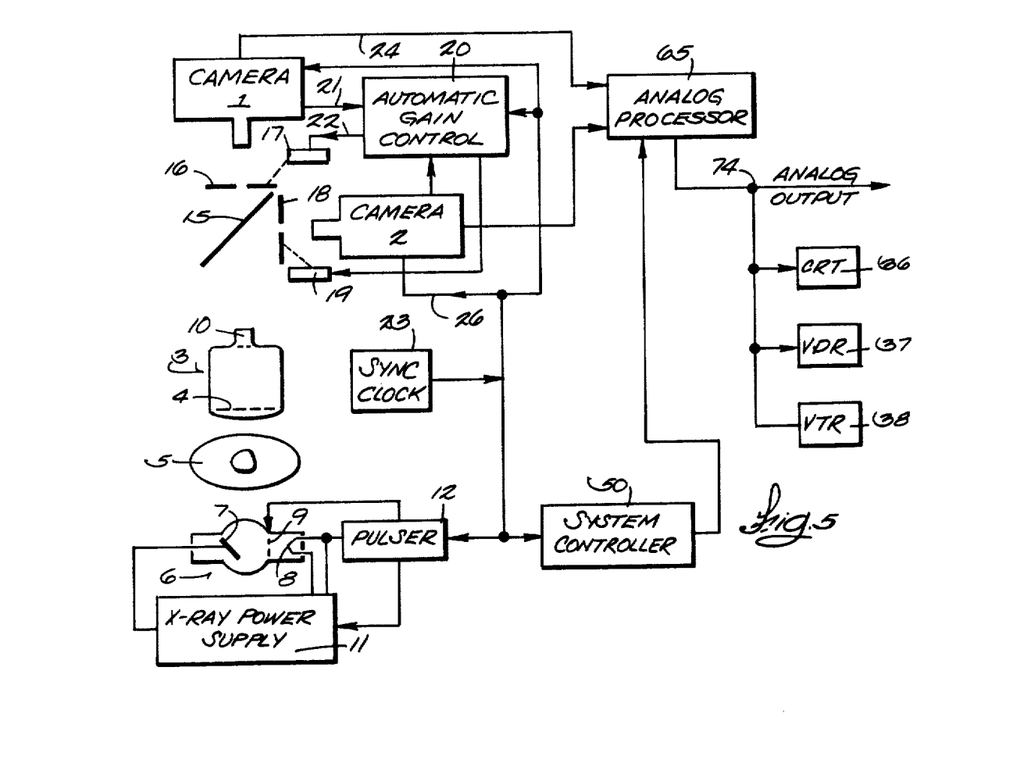
FIG. 5 is a two-channel subtraction system wherein the signals are processed in analog form.

FIG. 5 shows another embodiment of the dual pick-up device concept which uses analog signal processing methods and analog signal subtraction as compared with the FIGS. 1 and 3 embodiments which use digital processing. In FIG. 5, parts which are similar to those in FIGS. 1 and 3 are given the same reference numerals. In FIG. 5, the analog video signals resulting from scanning the image pick-up plate of camera 1 for the low energy x-ray pulse images are fed by way of a cable 24 to an analog processor which is represented by a block that is so labelled and marked with the reference numeral 65. Similarly, the analog video signals resulting from scanning the image pick-up plate of camera 2 are supplied by way of cable 26 to analog processor 64. The processor, which is shown schematically but in more detail in FIG. 8, has the capability for weighting and otherwise modifying the signals representative of the picture elements in the low and high x-ray energy view and for subtracting these signals to provide an analog video output signal which is representative of the subtraction image. In FIG. 8, analog processor 65 receives the raw video signals from the respective cameras in channels 1 and 2 and performs the following functions on each channel. In components 66 and 67 the respective incoming video signals are first offset and clamped. The respective analog signals are then coupled through buffer amplifiers 68 and 69 to the inputs of logarithmic or variable gamma amplifiers 70 and 71 where the signals are amplified logarithmically with offset and gain adjustment flexibility being provided for weighting. Buffer amplifiers 68 and 69 are operational amplifiers which have high input impedance and low output impedance for matching the input impedances of amplifiers 70 and 71 to the source impedance of the video signals. The signals in both channels are then fed to a differential amplifier 72 where in-phase video signals for the high and low energy x-ray images are combined or subtracted. A buffer operational amplifier 73 is used to match the subtraction video signals with the video output load represented by the coaxial cable 74. The analog video signals output cable is similarly identified by the numeral 74 in FIG. 5. Analog processor 65 also provides the composite sync signals for displaying the image resulting from subtraction on a cathode ray tube or TV monitor 36. The analog data representative of the subtraction images may also be recorded on video disk in the recorder represented by the block labelled VDR and 37 or on video tape in the recorder represented by the block labelled VTR and marked 38.

Figure 4:
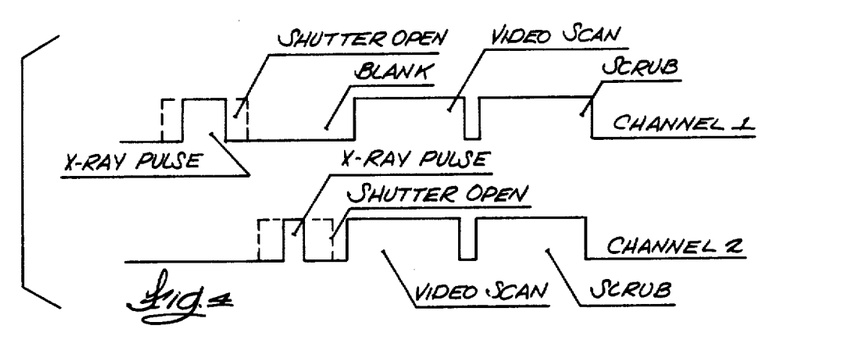
FIG. 4 is a timing diagram useful for explaining operation of the FIG. 3 system and, also, the FIG. 5 system, in the static imaging mode.

The timing diagram for the FIG. 5 system when it is operated in the static imaging mode is the same as is depicted in FIG. 4 which has already been described in connection with discussing the FIG. 3 embodiment and its operation in the static imaging mode.

The systems depicted in FIGS. 3 and 5 are also adapted for dynamic imaging. Timing for dynamic imaging will be discussed later in reference to FIG. 6. As implied earlier, dynamic imaging involves real-time display of events as they are occurring in the body being radiographed. In other words, motion studies can be made. Real-time, in connection with angiography, implies that the course of the x-ray opaque medium in the blood vessel is being observed continuously over a substantial interval such as twenty seconds or more. This requires developing data for a subtracted image at video rates which enable display on a standard video or TV monitor or recording on video disk or video tape for subsequent display. A real-time subtraction system requires both image pick-up devices to be scanned continuously according to the standard video rate which has 60 Hz interlaced fields if the power line frequency is 60 Hz for instance. The FIG. 3 embodiment, wherein digital processing is used, and the FIG. 5 embodiment, wherein analog processing is used, are operable in real-time mode in accordance with the timing diagrams depicted in FIG. 6.

Figure 6:
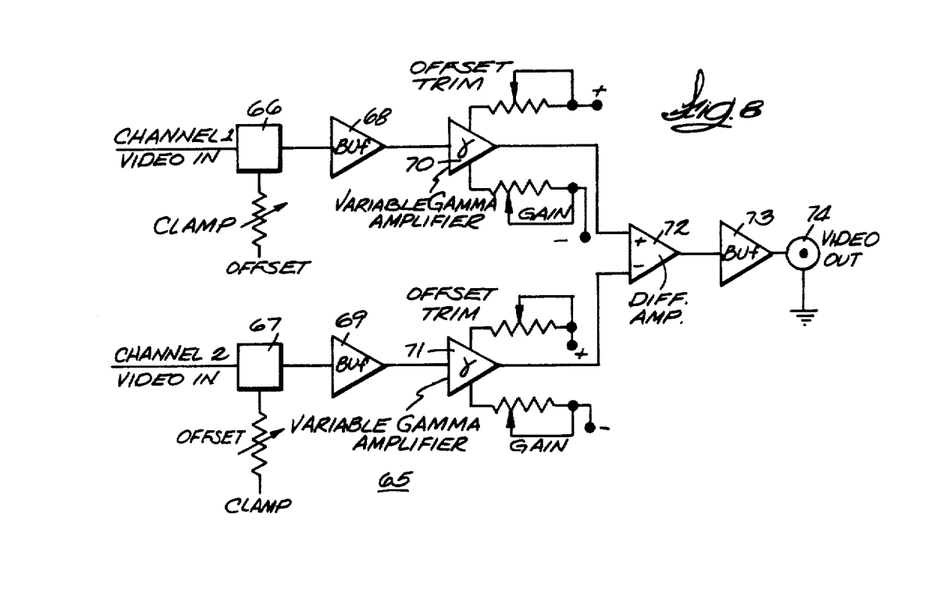
FIG. 6 is a timing diagram useful for explaining operation of the FIG. 5 and FIG. 3 systems when operating in the dynamic imaging mode.

Referring to FIG. 6, the x-ray tube kVp is switched at twice the power line frequency such as at a 120 Hz rate for producing subtracted images that can be displayed in real-time. The time between any clock pulse such as the one marked 80 and the next one marked 81 is 1/120th of a second in this example. Upon occurrence of the first clock pulse in the series, the low energy x-ray pulse, indicated by the dashed line marked 82, occurs. At this time the shutter 16 for camera 1 is open as indicated by the solid waveform 83. By the time the next clock pulse 81 occurs, the shutter for camera 1 is closed and readout or video scan of the image plate in camera 1 begins, as indicated by the timing waveform 84 in FIG. 6. The shutters or irises for the two cameras are closed and opened at the same rate to allow selective irradiation of the proper image pick-up plate but, of course, they are opened and closed alternately. The interval between clock pulses 80 and 81 in FIG. 6, for example, constitutes a delay period before video scanning of the camera 1 pick-up plate begins. In other words, camera 1 remains blanked during this period so the image plate in this camera serves as a temporary image storage element. When the next clock pulse 81 in a pair of successive clock pulses, such as the succession beginning with pulse 80, occurs, the high energy x-ray pulse 85 occurs at which time shutter for camera 2 is open for a short interval exceeding the duration of the x-ray pulse as indicated by the solid line timing waveform 86. Simultaneously with initiation of a high energy x-ray pulse 85, scan or readout of the image plate in camera 2 begins an indicated by the timing waveform 87 in the lowermost of the timing diagrams in FIG. 6. As can be seen, the two image pick-up plates of the cameras 5 are read out or scanned in phase so that a pair of 1/60th of a second fields, due to the respective low and high energy x-ray pulses are available from the cameras. Each field duration corresponds to the interval of two clock pulses which is equivalent to 1/60th of a second or, for example, the time between clock pulses 81 and 88 in the clock pulse timing diagram. The next pair of pulses produces another pair of fields and they are scanned for being interlaced with the preceeding respective fields. The data for the respective fields is sent through amplifiers 25 and 27, respectively, and to the digital processor 33 in the FIG. 3 embodiment or analog processor 65 in the FIG. 5 embodiment, as the case may be, wherein the data for the fields is weighted and subtracted and converted to a signal form for driving the CRT display to present the subtracted images as explained earlier. Then, as can be seen in the FIG. 6 timing diagram, a succession of low and high energy x-ray pulses continues to occur and for each pair of pulses there is a 1/60th of a second in-phase scan by each camera image pick-up plate to produce another pair of high and low energy fields which are subtracted in the processor and converted to a form for presentation as a single frame by the CRT, for example. The processors 33 and 65 in the respective FIGS. 3 and 5 embodiments provide the composite video timing signals for controlling the video monitor CRT and the video disk and video tape recorders VDR and VTR in a conventional manner for display or recording of the subtraction images as interlaced fields of which a pair constitutes a video frame. The processors may contain or have affiliated with them digital memories, not shown, for enabling frame integration and various signal modifications such as noise reduction and gray scale adjustment as was discussed earlier.

In summary, systems have been described for producing x-ray images represented by data that are weighted and subtracted to deemphasize anatomy that would otherwise obscure the anatomy of primary interest. The systems facilitate vascular studies since they provide improved contrast subtraction images when the x-ray opaque medium in the blood bessels is very dilute. This means that the medium can be injected into a vein remote from the site of interest and less of the medium than was formerly required needs to be used. The systems are also useful for obtaining subtraction images which enable differentiation of soft tissues that have little difference in their x-ray attenuation properties. The systems are based on use of two image pick-up devices in combination with a dual energy x-ray pulse source. In the illustrated system, two TV pick-up cameras are used in conjunction with an alternating kilovoltage generator to produce contrast-enhanced subtraction images that are free from motion artifacts. Limitations on image quality imposed by the characteristics of the video camera which prevail in prior art systems, wherein only one camera is used, are markedly mitigated. Static and dynamic or real-time images are obtainable.

Although various implementations of the multiple camera and multiple energy x-ray image subtraction system concept have been described in substantial detail in connection with static and dynamic imaging, such description is intended to be illustrated rather than limiting, for the concept can be variously implemented and is to be limited only by interpretation of the claims which follow.

We claim:

1. A method of producing data representative of an image resulting from combining of x-ray images including the steps of:

projecting from an x-ray source through a subject alternate x-ray beam pulses that have different energies to produce successive x-ray images, converting said x-ray images in coincidence with their occurrence to corresponding optical images, providing a first video camera means having image pick-up means for receiving the optical image corresponding to the one energy x-ray beam energy and a second video camera means having image pick-up means for receiving the optical image corresponding to the other energy x-ray beam energy, said pick-up means each responding to being scanned by producing analog video signals representative of the images, respectively, converting the analog video signals from the respective pick-up means to digital data corresponding to the respective images produced at the one and the other x-ray energies, storing the digital data corresponding to the image at one x-ray energy at least until the digital data corresponding to the other x-ray energy are obtained, and weighting the digital data representative of the respective images and combining the weighted digital data representative of the image at one energy with the data representative of the image at the other energy to yield digital data representative of the difference between the successive images.

2. The method set forth in claim 1 wherein each of said image pick-up means are scanned in the progressive mode to produce the analog video signals representative of the respective images.

3. The method set forth in any of claims 1 or 2 including the step of converting said digital data representative of the difference between images to analog video signals and supplying them to an analog storage device and to a television monitor which responds to said signals by displaying a visible difference image.

4. The method set forth in claim 1 including:

providing a shutter in the optical path to each image pick-up means and opening one shutter to pass the image corresponding to the one energy x-ray beam while the other shutter is closed and opening said other shutter to pass the image corresponding to the other energy x-ray beam while said one shutter is closed, controlling the x-ray source to produce the one and the other energy x-ray beam pulses while the shutters for passing their corresponding images are open, scanning one of the image pick-up means for a period after the one shutter is closed and during a part of which period the other shutter is open, then scanning the other of the image pick-up means for a period after its shutter is closed, and then scrubbing each image pick-up means for a period before occurrence of the next x-ray pulse.

5. The method set forth in claim 4 wherein the image pick-up means are scanned in the progressive scan mode.

6. The method set forth in claim 4 wherein the total time used for the x-ray pulses, the scanning periods and the scrubbing periods is such that a maximum of about 10 difference images per second can be produced.

7. A method of producing data representative of an image resulting from combining of x-ray images including the steps of:

projecting from an x-ray source through a subject alternate x-ray beam pulses that have different energies to produce successive x-ray images, converting said x-ray images in coincidence with their occurrence to corresponding optical images, providing a first image pick-up means for receiving the optical image corresponding to one x-ray beam energy and a second image pick-up means for receiving in sequence the optical image corresponding to the other x-ray beam energy, said image pick-up means responding to being scanned by producing analog video signals representative of the respective images, permitting the first pick-up means to store the image corresponding to one x-ray beam energy until the other pick-up means has received the image corresponding to the other x-ray beam energy and then scanning both pick-up means simultaneously to produce said analog video signals separately, converting the separate analog video signals simultaneously to digital data representative of the images produced with the one and the other x-ray energies, respectively, and weighting the digital data representative of the respective images and combining the weighted digital data representative of the image at one energy with the weighted data corresponding to the image at the other energy to yield digital data representative of the difference between the images.

8. The method set forth in claim 7 including the step of converting the digital data representative of the difference between the images to analog video signals and supplying them to an analog storage device and to a television monitor that responds by displaying a visible difference image.

9. The method set forth in claim 7 including:

providing a shutter in the optical path to each pick-up means and opening one shutter to pass the image corresponding to the one energy x-ray pulse while the other shutter is closed and opening said other shutter to pass the image corresponding to the other energy x-ray pulse while said one shutter is closed, and controlling the x-ray source to produce the one and the other energy x-ray pulses in successive pairs while the shutters are opened in succession, said scanning of the pick-up means occurring after both pulses in a pair occur, and scrubbing each pick-up means after it has been scanned and before the next x-ray pulse in a pair occurs.

10. The method set forth in any of claim 7, 8 or 9 wherein said cameras are scanned in the progressive scan mode.

11. The method set forth in claim 10 wherein the maximum number of difference images produced is about 10 per second.

12. The method set forth in claim 7 for dynamic imaging and including the steps of:

producing a series of clock pulses at a rate equal to twice power line frequency or any even multiple thereof, providing a shutter in the optical path to one and the other image pick-up means, opening and closing one shutter in substantial coincidence with occurrence of one clock pulse in the series and providing the x-ray pulse at one energy while said one shutter is open and before the next clock pulse in the series occurs, for the pick-up means to store the corresponding image as aforesaid, opening and closing the other shutter in substantial coincidence with occurrence of the next clock pulse in the series and providing the x-ray pulse at the other energy while said other shutter is open and before another one of said clock pulses occurs, and initiating concurrent scanning of both pick-up means in substantial coincidence with occurrence of said next clock pulse to produce said analog video signals.

13. The dynamic imaging method set forth in claim 12 wherein said clock pulse rate is 120 pulses per second and each of said pick-up means are scanned in substantially one-sixtieth of a second and the successive scans for each pick-up means are interlaced such that difference images are produced at a rate of 30 frames per second.

14. A method of producing data representative of an image resulting from combining x-ray images including the steps of:

projecting from an x-ray source through a subject alternate x-ray beam pulses that have different energies to produce successive x-ray images, converting said x-ray images in coincidence with their occurrence to corresponding optical images, providing a first image pick-up means for receiving the optical image corresponding to one x-ray beam energy and a second image pick-up means for receiving in sequence the optical image corresponding to the other x-ray beam energy, said pick-up means responding to being scanned by producing analog video signals representative of the respective images, permitting the first pick-up means to store the image corresponding to one x-ray beam energy until the other pick-up means has received the image corresponding to the other x-ray beam energy and then scanning both pick-up means simultaneously to produce said analog video signals separately, and weighting the analog video signals corresponding to the respective low and high energy images and combining the weighted signals to yield analog signals representative of the difference between the images.

15. The method set forth in claim 14 including:

providing a shutter in the optical path to each image pick-up means and alternately opening one shutter to pass the image corresponding to the one energy x-ray pulse while the other shutter is closed and opening said other shutter to pass the image corresponding to the other energy x-ray pulse while said one shutter is closed, and controlling the x-ray source to produce the one and the other energy x-ray pulses in successive pairs while the shutters are opened alternately, said scanning of the pick-up means occurring after both pulses in a pair occur, and scrubbing each pick-up means after it has been scanned and before the next x-ray pulse in a pair occurs.

16. The method set forth in any of claims 14 or 15 wherein said pick-up means are scanned in the progressive scan mode.

17. The method set forth in claim 16 wherein the maximum number of difference images produced is about 10 per second.

18. The method set forth in claim 14 for dynamic imaging and including the steps of:

producing a series of clock pulses at a rate equal to an even multiple of power line frequency, providing a shutter in the optical path to one and the other image pick-up means, opening and closing one shutter in substantial coincidence with occurrence of one clock pulse in the series and providing the x-ray pulse at one energy while said one shutter is open and before the next clock pulse in the series occurs, for the one pick-up means to store the corresponding image as aforesaid, opening and closing the other shutter in substantial coincidence with occurrence of the next clock pulse in the series and providing the x-ray pulse at the other energy for said other pick-up means to receive an image while said other shutter is open and before another one of said clock pulses occurs, and initiating concurrent scanning of both pick-up means in substantial coincidence with occurrence of said next clock pulse to produce said analog video signals.

19. The method set forth in claim 18 wherein said power line frequency is 60 Hz and the clock pulse rate is 120 pulses per second and each of said pick-up means are scanned in substantially one-sixtieth of a second.

20. Diagnostic x-ray apparatus including an x-ray source, means operative to control said x-ray source to emit successive pairs of x-ray beam pulses, the pulses in a pair having different energies, said beams being projected through a body under examination to produce successive pairs of different energy x-ray images of a portion of said body through which said beams project, means for converting said x-ray images to corresponding optical images, and improved means for combining one image in a pair with the other comprising:

first and second optical image pick-up means arranged for one of said pick-up means to receive optical images corresponding to high energy x-ray pulses and the other of said pick-up means to receive optical images corresponding to lower energy x-ray pulses, said pick-up means each being operative to convert said received images to analog video output signals representative of the different energy images, respectively, and signal processing means including means for weighting the signals representative of the respective low and high energy images and combining the signals corresponding to the signals representative of the image made at one x-ray energy with the signals representative of the next image made at the other x-ray energy to thereby provide signals representative of the weighted difference between said images in a pair.

21. The apparatus set forth in claim 20 including:

shutter means interposed in each of the optical paths between said image converting means and the pick-up means, respectively, and means for operating said shutter means synchronously with occurrence of the x-ray pulses for said first pick-up means to receive the optical image corresponding to one energy x-ray pulse in a pair while said second pick-up means is blocked, and for said second pick-up means to receive the optical image corresponding to the other energy x-ray pulse in a pair while said first pick-up means is blocked.

22. The apparatus as in any of claims 20 or 21 including:

analog-to-digital converter means for converting the successive video signals from the respective pick-up means to digital data representative of the picture elements comprising the images produced with the respective different energy x-ray pulses, first and second memory means and means for directing the digital data representative of an image in a pair corresponding to one x-ray energy to one of said memory means and the digital data representative of the image corresponding to the other x-ray energy to the other of said memory means.

said signal processing means comprising digital data processor means having input means for receiving the digital data from the memories and having output means for the digital data representative of the image resulting from subtraction.

23. The apparatus as in any of claims 20 or 21 wherein said analog video signals from each image pick-up means are obtained by reading out each pick-up means in the progressive scan mode.

24. The apparatus as in claim 22 including:

multiplexer means having input and output means, the input means being coupled to the pick-up means for receiving the analog video signals representative of the different x-ray energy images in sequence, the output means being coupled to said analog-to-digital converter means, said multiplexer means being operative to provide the image representative analog signals sequentially to said converter means, said means for directing the digital data including another multiplexer means having input means coupled to said converter means and output means coupled to said memory means.

25. Diagnostic x-ray apparatus including an x-ray source, means operative to control said x-ray source to emit successive pairs of x-ray beam pulses, the pulses in a pair having different energies, said beams being projected through a body under examination to produce successive corresponding pairs of different energy x-ray images of a portion of said body through which said beams project, means for converting said x-ray images to corresponding optical images, and improved means for combining one image in a pair with the other comprising:

first and second image pick-up means for respectively receiving the optical images corresponding to the successive different energy x-ray images in a pair, each of said pick-up means being subject to scanning to produce analog video signals representative of the optical image it has last received, shutter means for each pick-up means and means for actuating said shutter means and for effecting scanning of said pick-up means in a time relationship such that said one pick-up means is prevented from receiving the image corresponding to one x-ray energy while the other pick-up means receives it and the other pick-up means is prevented from receiving the image corresponding to the other x-ray energy while said one pick-up means receives it and while said other pick-up means still stores its image, and scanning of each of said pick-up means occurs in phase to produce said analog video signals for images in a pair simultaneously, and signal processing means including means for weighting signals corresponding to the respective images in a pair and means for combining the weighted signals to provide signals corresponding to the difference between said images.

26. Diagnostic x-ray apparatus including an x-ray source, means operative to control said source to emit successive pairs of x-ray beam pulses, alternate pulses in a pair having different energies, said beams being projected through a body under examination to produce successive pairs of different energy x-ray images, means for converting said x-ray images to optical images, and improved means for combining one image in a pair with another, comprising:

first and second image pick-up means for respectively receiving the optical images corresponding to the different energy images in a pair, of each of said pick-up means being operable in a scanning mode that results in producing analog video signals representative of the image it has last received, shutter means disposed in each of the paths from the image converting means to the respective pick-up means, means for actuating said shutter means in a time relationship such that the second pick-up means is prevented from receiving the image corresponding to one x-ray energy while the first pick-up means receives it and the first pick-up means is prevented from receiving the image corresponding to the other x-ray energy while the second pick-up means receives it, and while said first pick-up means still stores its image, means for initiating scanning of said first and second pick-up means concurrently for said producing of the analog signals representative of the respective different energy images, first and second analog-to-digital converter means for respectively converting the analog video signals representative of the different energy images to corresponding digital data, digital processor means coupled to the respective analog-to-digital converter means and being operative to weight the digital data representative of each image and to combine the weighted digital data corresponding to the image produced at one x-ray energy with the weighted data corresponding to the image produced at the other x-ray energy to yield digital data representative of the difference between said images in a pair.

27. The apparatus as in claim 26 including a digital-to-analog converter for converting the yielded digital data to analog video signals.

28. The apparatus as in claim 26 adapted for static imaging wherein said pick-up means are scanned in the progressive scan mode.

29. The apparatus as in claim 26 adapted for dynamic imaging wherein said pick-up means are scanned in the interlaced mode.

30. The apparatus as in claim 26 including:

means for producing a series of clock pulses at a rate that corresponds to an even multiple of power line frequency, occurrence of one in the series of clock pulses corresponding to opening and closing of the shutter for one pick-up means and to production of an x-ray pulse having the one energy while said shutter is open for said one pick-up means to receive and store an image, occurrence of the next in said series of clock pulses corresponding to opening and closing of the shutter for the other pick-up means and to production of an x-ray pulse having the other energy while said shutter is open, and said occurrence of said next pulse corresponding substantially to initiating simultaneous scanning of both pick-up means.

31. The apparatus as in claim 30 wherein said power line frequency is 60 Hz and said clock pulse rate is 120 Hz and the simultaneous scanning occurs in one-sixtieth of a second.

32. The apparatus as in claim 28 wherein after each of said pick-up means are scanned concurrently each of said cameras are scrubbed before another x-ray pulse occurs 33. Diagnostic x-ray apparatus including an x-ray source, means operative to control said source to emit successive pairs of x-ray beam pulses, alternate pulses in a pair having different energies, said beams being projected through a body under examination to produce successive pairs of different energy x-ray images, means for converting said x-ray images to optical images, and improved means for combining one image in a pair with the other, comprising:

first and second image pick-up means for respectively receiving the optical images corresponding to the different energy images in a pair, each of said pick-up means being operable in a scanning mode that results in producing analog video signals representative of the image it has last received, shutter means disposed in each of the optical paths from the image converting means to the respective pick-up means, means for actuating said shutter means in a time relationship such that the second pick-up means is prevented from receiving the image corresponding to one x-ray energy while the first pick-up means receives it and the first pick-up means is prevented from receiving the image corresponding to the other x-ray energy while the second pick-up means receives it, and while said first pick-up means still stores its image, means for initiating scanning of said first and second pick-up means concurrently for said producing of the analog video signals representative of the respective different energy images, and analog processor means for weighting the analog signals representative of the respective different energy images and combining the weighted analog signals corresponding to the image obtained with one x-ray energy with the weighted analog video signals corresponding to the image obtained at the other x-ray energy to thereby yield analog signals representative of the difference between the images.

34. The apparatus as in claim 33 wherein said analog video signals from each pick-up means are obtained by scanning each pick-up means in the progressive scan mode.

35. The apparatus as in claim 33 adapted for dynamic imaging wherein said pick-up means are scanned in the interlaced mode.

36. The apparatus as in claim 33 including:

means for producing a series of clock pulses at a rate that corresponds to an even multiple of power line frequency, occurrence of one in the series of clock pulses corresponding to opening and closing of the shutter for one pick-up means and to production of an x-ray pulse having the one energy while said shutter is open for said one pick-up means to receive and store an image, occurrence of the next in said series of clock pulses corresponding to opening and closing of the shutter for the other pick-up means and to production of an x-ray pulse having the other energy while said shutter is open, and said occurrence of said next pulse corresponding substantially to initiating simultaneous scanning of both pick-up means.

37. The apparatus as in claim 33 wherein said power line frequency is 60 Hz and said clock pulse rate is 120 Hz and the simultaneous scanning occurs in one-sixtieth of a second.

* * * * *